United States Patent [19]

Hofmann

[11] Patent Number: 4,936,863
[45] Date of Patent: Jun. 26, 1990

[54] HIP PROSTHESIS

[76] Inventor: Aaron A. Hofmann, 1349 E. Princeton Ave., Salt Lake, Utah 84105

[21] Appl. No.: 193,571

[22] Filed: May 13, 1988

[51] Int. Cl.⁵ .......................... A61F 2/32; A61F 2/30
[52] U.S. Cl. ......................................... 623/23; 606/66
[58] Field of Search ................. 623/16, 18, 20, 22, 623/23; 128/92 Y, 92 YZ, 92 YY, 92 YQ

[56] References Cited

U.S. PATENT DOCUMENTS

| 3,840,904 | 10/1974 | Tronzo | 623/18 |
|---|---|---|---|
| 3,916,451 | 11/1975 | Buechel et al. | 623/18 |
| 3,977,026 | 8/1976 | Battault | 623/18 |
| 3,986,212 | 10/1976 | Sauer | 623/18 |
| 4,011,602 | 3/1977 | Bybicki et al. | 623/18 |
| 4,038,703 | 8/1977 | Bokros | 623/16 |
| 4,141,088 | 2/1979 | Treace et al. | 623/16 |
| 4,164,794 | 8/1979 | Spector et al. | 623/16 |
| 4,261,351 | 4/1981 | Scherfel | 128/92 YZ |
| 4,328,593 | 5/1982 | Sutter et al. | 623/18 |
| 4,355,428 | 10/1982 | Deloison et al. | 623/18 |
| 4,385,405 | 5/1983 | Teinturier | 623/23 |
| 4,430,761 | 2/1984 | Niederer et al. | 623/23 |
| 4,549,319 | 10/1985 | Meyer | 623/23 |
| 4,645,506 | 2/1987 | Link | 623/23 |
| 4,756,711 | 7/1988 | Mai et al. | 623/23 |
| 4,775,381 | 10/1988 | Tari et al. | 128/92 YZ |

FOREIGN PATENT DOCUMENTS

| 560587 | 9/1957 | Belgium | 128/92 YZ |
|---|---|---|---|
| 0169978 | 2/1986 | European Pat. Off. | 623/22 |
| 0266081 | 5/1988 | European Pat. Off. | 623/22 |
| 2941265 | 4/1980 | Fed. Rep. of Germany | 623/23 |
| 3528151 | 2/1987 | Fed. Rep. of Germany | 623/23 |
| 2416004 | 10/1979 | France | 623/18 |
| 2549717 | 2/1985 | France | 623/22 |
| 2153233 A | 8/1985 | United Kingdom . | |

Primary Examiner—David J. Isabella
Attorney, Agent, or Firm—Kelly, Bauersfeld & Lowry

[57] ABSTRACT

An improved prosthetic device is provided particularly such as a hip prosthesis for surgical implantation into a patient. The hip prosthesis comprises an improved femoral component having an upwardly and laterally open slot formed in an upper region thereof to permit compression of the femoral component to a reduced size configuration for easier installation into a resected patient femur. An improved installation tool cooperates with the femoral component for compressing and holding the femoral component in the reduced size configuration during installation, and then for releasing the femoral component for expansion to a tight fit within the patient bone. An antirotation fin is insertable into the slot of the implanted femoral component to maintain the femoral component in the expanded state. A portion of the antirotation fin may bridge into adjacent patient bone for improved prosthesis fixation against rotation. An improved acetabular component is also provided in a size for relatively easy implantation into the acetabulum, followed by insertion of a slightly oversize acetabular bearing member which expands the acetabular component sufficiently for tight fit within the acetabulum.

13 Claims, 5 Drawing Sheets

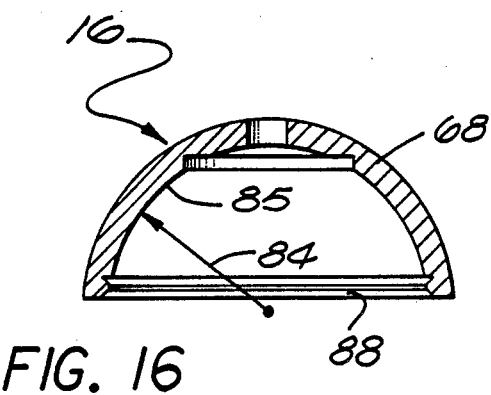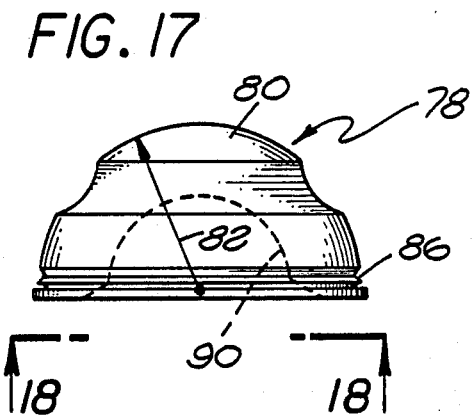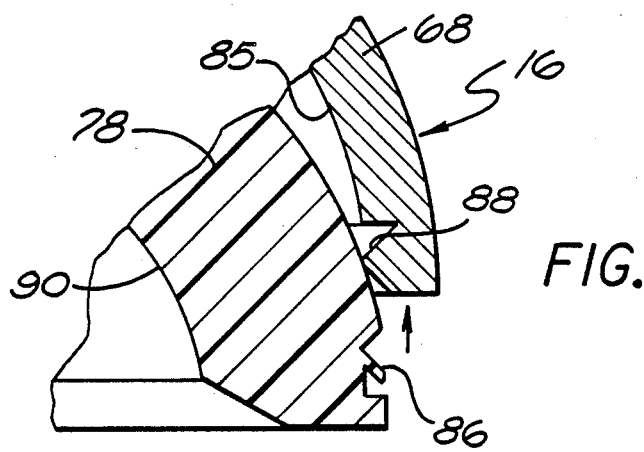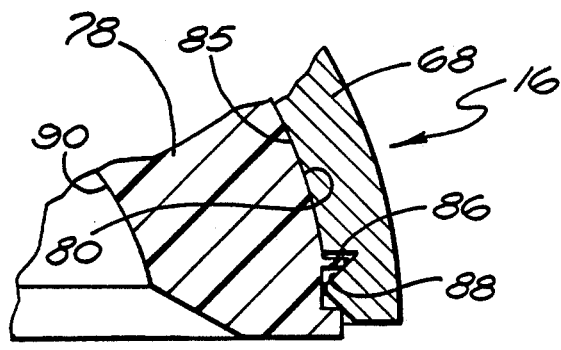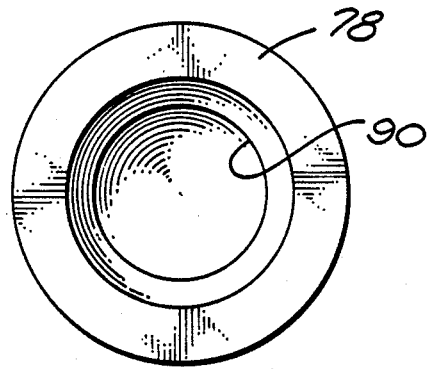

HIP PROSTHESIS

BACKGROUND OF THE INVENTION

This invention relates generally to improvements in prosthetic devices, particularly such as hip prostheses and the like. More specifically, this invention relates to an improved prosthesis and related installation tool and method designed to achieve improved tight prosthesis fixation with respect to patient bone, without requiring the use of bone cement for fixation purposes.

Artificial or prosthetic devices for implantation into animals, particularly humans, have been the subject of extensive research and development efforts for many years. Such prosthetic devices have typically comprised one or more implant components formed from a relatively biostable material having selected structural properties and unique shapes to replace all or part of selected bone structures, such as an anatomical joint including, for example, a hip joint. The implant components are installed by surgical access to the subject bone or joint region and by resection of one or more bone surfaces to accommodate direction implant component attachment to the bone.

More specifically, in the context of a hip prosthesis, the hip joint of a patient is accessed surgically to permit removal of the head and neck of the patient's femur to expose the internal medullary canal. A prosthetic component having an artificial femoral head and neck is then implanted by seating an elongated stem of the prosthetic component into the medullary canal. In some procedures, a second prosthetic component is implanted into the patient's acetabulum and cooperates with a typically plastic bearing member to engage the femoral component and thereby form a reconstructed artificial hip joint. In the past, the femoral and/or acetabular prosthetic components have been secured to adjacent patient bone by use of bone cements, such as a methyl methacrylate based cement or the like which interdigitates with the interstices of bone surfaces to achieve mechanical prosthesis fixation.

In recent years, a variety of disadvantages and limitations have been recognized in connection with cemented fixation of prosthetic devices. More particularly, it is now generally recognized that the use of bone cement provides a temporary securement which is relatively weak from a structural standpoint and thereby normally requires significant postoperative patient restrictions to avoid failure of the cemented interface during the patient's lifetime. Failure of the cemented interface is especially undesirable, since the bone cement contributes to localized bone embrittlement and loss of structure such that implantation of a secondary prosthesis can be extremely difficult and sometimes impossible. These problems encountered with cemented prostheses are particularly severe in high load bearing, highly stressed patient joints, such as a hip joint.

In an effort to avoid use of bone cement for prosthesis fixation, a variety of improved prosthetic devices have been developed in recent years for noncemented fixation to patient bone. Many of these improved devices have utilized attachment surfaces of carefully controlled porosity characteristics designed for direct bone attachment by ingrowth or resorption of living cancellous bone or tissue. However, while these bone ingrowth proposals appear to offer significant advantages over prior cemented designs, various problems have still been encountered with respect to insuring positive and stable prosthesis fixation especially at highly loaded and stressed joints, such as the hip. For example, for proper fixation, a relatively tight press-fit relation between the prosthesis and the bone must be obtained and maintained. Any significant movement of the prosthesis relative to the bone during a prolonged postoperative ingrowth period can result in permanent loosening and eventual failure of the prosthesis.

Unfortunately, due to the infinite variation in the size and shape of patient bones and the relatively inexact methods used for bone resection, it is extremely difficult for the surgeon to obtain consistent tight press-fit installation of a prosthesis relative to patient bone. Moreover, although an adequate tight fit of a prosthesis may be apparent during surgery, the surgeon has no effective way to quantify the degree of tight fit, whereby the surgeon cannot know with certainty that a proper prosthesis fit has been achieved. Efforts to overcome these problems have been addressed most often by attempting to implant an oversize prosthesis into an undersize medullary canal or the like. However, this procedure can be extremely difficult and increases the risk of fracturing patient bone during the implantation surgery.

There exists, therefore, a significant need for an improved prosthetic device particularly such as an improved prosthetic hip joint, wherein the prosthetic device is designed for relatively easy implantation into a resected patient bone or the like without significant press-fitting and thereafter expanded in a reliable manner to achieve a relatively strong press-fit interconnection with patient bone. The present invention fulfills these needs and provides further related advantages.

SUMMARY OF THE INVENTION

In accordance with the invention, an improved prosthesis device particularly such as a hip prosthesis is provided for facilitated implantation into a patient in a position for secure and stable attachment to patient bone. The prosthetic device includes a portion thereof adapted to assume a reduced size configuration for ease of implantation, for example, into the medullary canal of patient bone. The implanted prosthetic device is then expanded to a larger size for highly secure press-fit attachment to the bone. The improved prosthetic device is particularly adapted for inclusion of one or more porous ingrowth surfaces which mechanically interlock with patient bone over a period of time.

In a preferred form of the invention, the prosthetic device comprises a femoral component of a hip prosthesis. The femoral component is formed from a biocompatible high strength material, such as titanium or titanium alloy, to have an elongated stem with a general size and shape to fit into the medullary canal of a resected patient femur. An upper region of the stem is enlarged and contoured to correspond with the general medullary canal shape and is joined to an upwardly extending neck adapted to carry a generally spherical or ball-shaped head. The upper region of the stem includes a generally longitudinally extending slot formed therein, preferably in a position with the slot opening upwardly and in a lateral or outboard direction relative to the patient's leg when the femoral component is implanted.

The slot in the upper region of the femoral component permits the upper region to be compressed to a smaller profile in the anterior-posterior direction by squeezing the upper region inwardly on the opposite sides of the slot. In this regard, a femoral component of titanium or titanium alloy has a high Young's modulus and requires a substantial force to compress the femoral component to the reduced profile, but this material also exhibits a high degree of elasticity for return substantially to its initial nondeformed shape when released. Accordingly, the upper region of the femoral component is compressed to the reduced size and implanted in that condition, after which the upper region is released to permit the upper region to return to its initial nondeformed shape in tight press fit engagement with patient bone. A slot width as small as a few millimeters is effective to provide a sufficiently reduced profile for easy implantation yet fit tightly against the patient bone when released for return to the nondeformed state.

An improved femoral component installation tool is provided for holding the femoral component in the reduced size configuration during implantation and thereafter releasing the femoral component for expansion substantially to the nondeformed state. The installation tool includes a threaded tip for thread-in engagement with an upwardly open threaded bore formed in the upper region of the femoral component. As the tip advances into the threaded bone, a pair of ramped yoke fingers on the installation tool are drawn into clamping engagement respectively with the anterior and posterior faces such as recessed ramped tracks formed on the femoral component upper region. The yoke fingers thus squeeze the upper region to the reduced size profile for easy implantation. After the femoral component is properly positioned within the patient bone, the tool tip and yoke fingers are retracted and released from the femoral component to permit component expansion.

After implantation, an antirotation fin is fitted into the slot in the femoral component. This antirotation fin advantageously fills the slot to prevent possible loosening of the femoral component in response to complex mechanical loads during normal patient movements which might otherwise compress the femoral component back toward its reduced profile configuration. Moreover, the fin beneficially protrudes from the lateral margin of the femoral component to interlock with patient bone, thereby securely locking the implanted femoral component against rotation.

In another preferred form, an acetabular component is provided for use, for example, with a femoral component of the type described above. The acetabular component is formed from a high strength material such as titanium or titanium alloy to have a generally hemispherical shape with a normal outer diametric size for relatively easy implantation into a prepared patient acetabulum. A radial segment of the acetabular component is removed to define a radial recess permitting the general diametric size of the acetabular component to be increased. A generally cup-shaped bearing member of conventional plastic bearing material or the like is seated into the implanted acetabular component, wherein this bearing member is slightly oversize relative to the acetabular component. The bearing member thus expands the diametric size of the acetabular component slightly but sufficiently to achieve a tight press-fit within the acetabulum. A general semispherical cavity in the bearing member receives the ball-shaped head of the femoral component to permit normal postoperative patient movement.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 13 is an enlarged sectional view similar to FIGS. 10 and 11 but depicting the antirotation fin inserted into the femoral component;

FIG. 16 is a vertical sectional view illustrating the cross-sectional geometry of the acetabular component;

FIG. 17 is a side elevation view depicting the acetabular bearing member;

FIG. 18 is bottom plan view of the acetabular bearing member, taken generally on the line 18—18 of FIG. 17;

FIG. 19 is an enlarged fragmented sectional view depicting movement of the acetabular bearing member toward seated and interlocked engagement with the acetabular component; and FIG. 20 is an enlarged fragmented sectional view similar to FIG. 19 but showing the acetabular bearing member seated within the acetabular component.

DETAILED DESCRIPTION OF THE PREFERRED EMBODIMENTS

Figure 1:
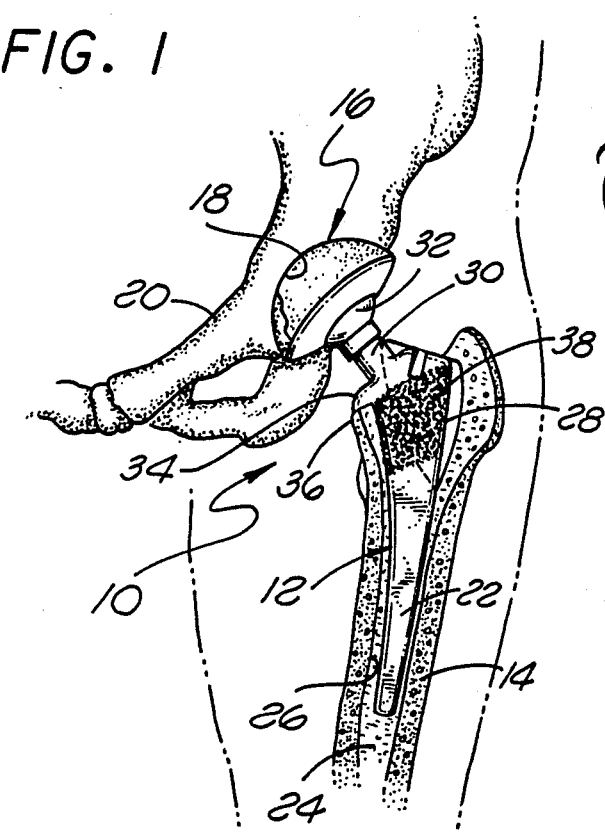
FIG. 1 is a fragmented perspective view illustrating an improved hip prosthesis embodying the novel features of the invention.

As shown in the exemplary drawings, an improved prosthetic device is provided for enhanced ease of implantation with improved strength of attachment to patient bone. As shown generally in FIG. 1, a preferred form of the invention comprises an improved hip prosthesis referred to generally by the reference numeral 10. The hip prosthesis 10 includes a femoral component 12 adapted for implantation and affixation relative to the upper end of a patient's femur bone 14, in combination with an acetabular component 16 adapted for implantation and affixation relative to the acetabulum 18 of a patient's pelvic bone 20. In both cases, the prosthetic components are designed for initial implantation in a reduced profile or size, followed by expansion to a larger profile or size to achieve a desired tight and stable mechanical interlock with patient bone.

The prosthetic device of the present invention is designed particularly for secure fixation to patient bone without requiring the use of traditional bone cements for fixation purposes. Both the femoral and acetabular components 12 and 16 are designed to assume a relatively reduced profile or size to assure facilitated implantation into a prepared bone cavity. This configuration in a reduced size or profile effectively safeguards against risk of bone fracture during implantation and further assures a more rapid implantation procedure with reduced trauma to the patient. Once the prosthetic device is seated in the desired position within the prepared bone cavity, the prosthetic device is adapted for expansion to fit tightly against the patient bone with a controlled and predetermined fixation force. This provides a substantially maximized mechanical interlock with the patient bone, whereby the invention is particularly suited for use with porous bone ingrowth surfaces to achieve a further enhanced bone interlock over a period of time during postoperative recovery.

Figure 7:
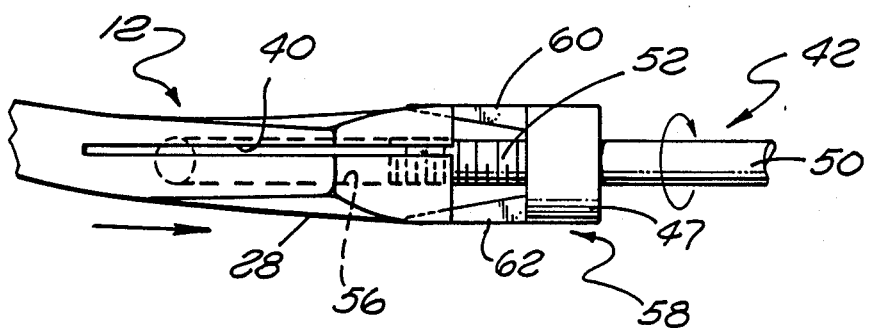
FIG. 7 in an enlarged, fragmented plan view depicting initial installation tool movement into partial engagement with the femoral component.

The femoral component 12 is shown in more detail in a preferred form in FIGS. 1-13. As shown, the femoral component comprises an elongated stem 22 having a size and shape to fit within a resected upper end of a patient's femur 14. In this regard, the stem 22 is generally straight to have a length typically on the order of one-third the length of the femur 14, and is provided with a noncircular cross-sectional shape such as the illustrative generally rectangular shape for secure locking within cancellous bone 24 (FIG. 1) disposed within and lining the medullary canal 26 of the femur. The upper end of the stem 22 is joined integrally with an enlarged upper region 28 which has a size and a generally anatomically contoured shape to seat securely within the uppermost end of the resected bone. This upper region 28 may be slightly angled anteriorly relative to the stem 22 for better anatomical fit, as viewed best in FIGS. 4, 7 and 8, and is joined in turn to an upwardly extending neck 30 adapted to carry a generally ball-shaped head 32.

The femoral component 12 described thus far is generally conventional in terms of overall size and shape, it being understood that a wide variety of geometrical variations may be incorporated into the device according to the specific needs of the patient. The femoral component is implanted by surgical access to the hip joint for conventional resection of the femur 14 to expose the upper end of the medullary canal 26 therein. The medullary canal 26 is appropriately broached and reamed to permit seating of the prosthesis stem 22 within the canal in tight, press-fit engagement with the patient bone. When seated, an upper lip 34 on the femoral component upper region 28 is commonly provided to overlay the upper end of the resected bone to rest at least partially upon the harder external cortical bone 36 (FIG. 1). A depending antirotation pin 35 is advantageously provided on the lip 34 to penetrate the adjacent bone for purposes of resisting prosthesis rotation during normal postoperative patient function. In the preferred form, at least a portion of the exterior surface of the femoral component, and particularly the upper region 28 as shown in the exemplary drawings, is lined with a selected porous bone ingrowth material 38 for appropriate postsurgical ingrowth of bone or other patient tissue over a period of time. Such bone ingrowth surfaces are well known to those skilled in the art and are exemplified, for example, by the structures shown and/or described in U.S. Pat. Nos. 3,986,212; 3,977,026; 4,164,794; and 4,355,428.

In accordance with one primary aspect of the invention, the upper region 28 of the femoral component 12 is adapted for deformation to a reduced size or profile configuration to permit easier implantation to the desired position seated within the resected femur 14. Once implanted, however, the upper region is expanded to a larger size profile for achieving a high strength press-fit connection with the patient bone. In this manner, a significantly tighter prosthesis interlock with the femur can be achieved to safeguard against the prosthesis becoming loose during normal patient function. This tighter prosthesis/bone interlock advantageously retains the prosthesis without significant movement with respect to patient bone such that the use of a fixation cement is not required and further such that a more secure bone ingrowth interlock will eventually result. Moreover, and perhaps most importantly, the femoral component 12 is secured tightly to the patient bone irrespective of minor bone size variations and inaccuracies inherent in the resection procedure.

Figure 2:
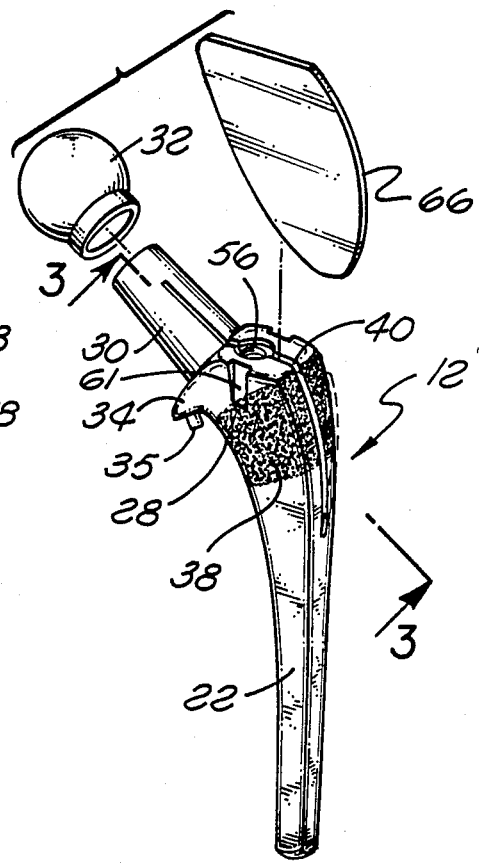
FIG. 2 is an exploded perspective view depicting the construction and assembly of a femoral component for the hip prosthesis.
Figure 3:
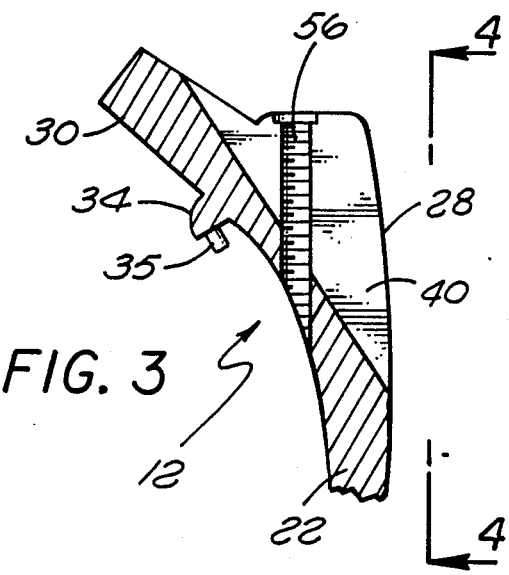
FIG. 3 is an enlarged, fragmented vertical sectional view taken generally on the line 3—3 of FIG. 2.
Figure 4:
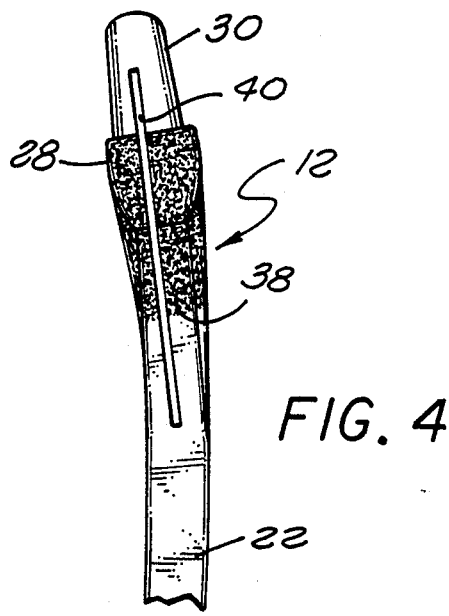
FIG. 4 is a fragmented lateral side elevation view taken generally on the line 4—4 of FIG. 3.
Figure 5:
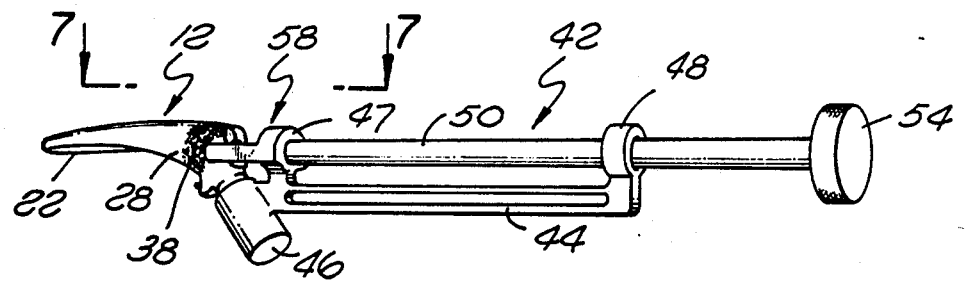
FIG. 5 is a perspective view depicting an improved installation tool engaged with the femoral component of FIGS. 2-4.
Figure 6:
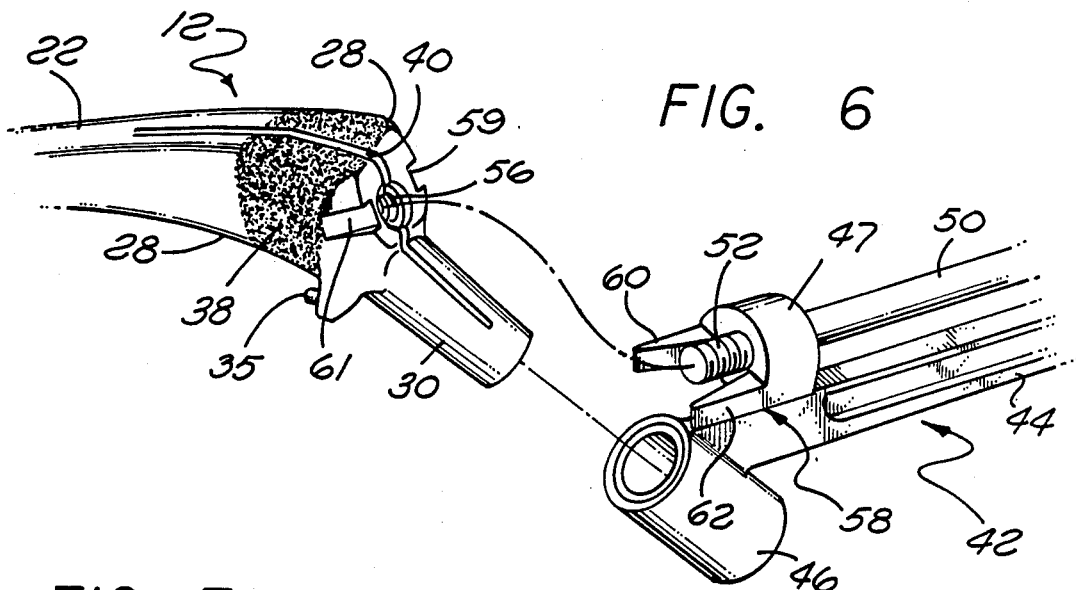
FIG. 6 is an enlarged, fragmented and exploded perspective view showing engagement of the installation tool with the femoral component.

As shown in FIGS. 2-4, the deformation capability in the femoral component upper region 28 is provided by means of an elongated and generally longitudinally oriented slot 40 formed in the upper region 28. This slot 40 is formed in the lateral or outboard side edge of the femoral component 14 to permit the side edges on opposite sides of the slot to be compressed or pressed together a short distance in the anterior-posterior direction. In this regard, the entire femoral component 12 is constructed from a high strength yet biocompatible material capable of withstanding the various mechanical loads to be encountered during normal use. Moreover, the selected material is chosen for the capability to undergo the above-referenced compression to a reduced size profile for facilitated implantation, with substantially elastic properties for return to the nondeformed state when released after implantation. A titanium or titanium alloy prosthesis material is preferred to fulfill these physical characteristics.

An improved installation tool 42 is provided for securely supporting and holding the femoral component 12 in the reduced profile configuration during implantation. More particularly, as viewed in FIGS. 5-9, the installation tool 42 comprises an elongated frame 44 supporting an angularly set socket cap 46 sized to seat firmly over the neck 30 of the prosthesis. A pair of support arms 47 and 48 on the frame 44 support a lock rod 50 for rotation therein without axial advancement. A forward end of this lock rod 50 protrudes beyond the forward frame support arm 47 to terminate in threaded guide tip 52. An enlarged turning knob 54 is provided at the rear end of the lock rod 50 for manually rotating the lock rod 50 inclusive of the threaded guide tip 52. Accordingly, the lock rod 50 can be manually rotated to advance the threaded tip 52 into engagement with an upwardly open threaded bore 56 formed in the upper region 28 of the femoral component. Importantly, advancement of the guide tip 52 threadably into the bore 56 simultaneously draws the prosthesis upper region 28 into clamped relation with a yoke 58 on the frame support arm 47. In this regard, the yoke 58 includes a spaced pair of yoke fingers 60 and 62 having ramped inboard faces for engaging the anterior and posterior sides of the prosthesis within ramped recessed guide tracks 59 and 61 (FIG. 6) to compress the side edges of the prosthesis upper region 28 together as the guide tip 52 seats within the bore 56. The prosthesis is thus compressed by the yoke fingers 60 and 62 to a reduced size or reduced profile configuration in the anterior-posterior direction. Alternately, if desired, other types of clamping mechanisms adapted to perform a similar function can be used.

Figure 8:
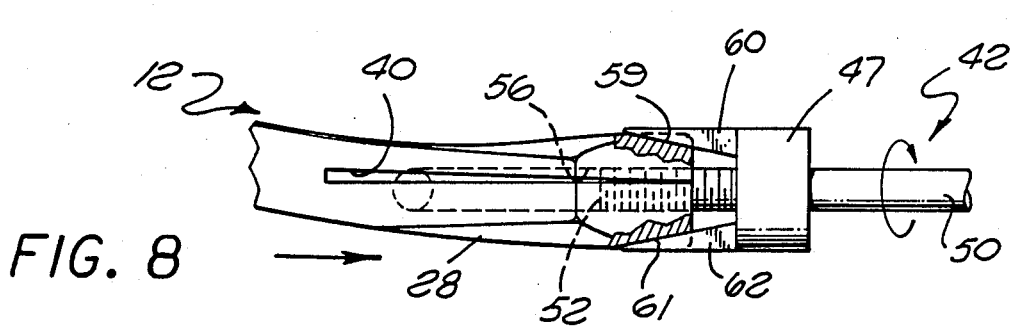
FIG. 8 is an enlarged, fragmented plan view similar to FIG. 7 but depicting full engagement between the installation tool and the femoral component.
Figure 9:
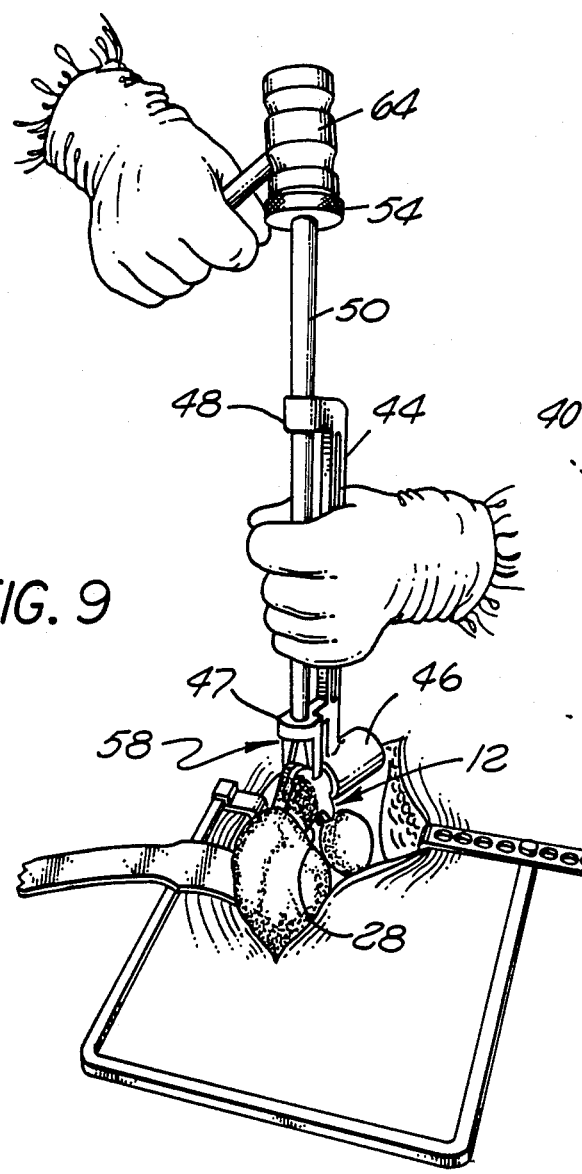
FIG. 9 is a perspective view depicting use of the installation tool in surgery for placement of the femoral component.
Figure 12:
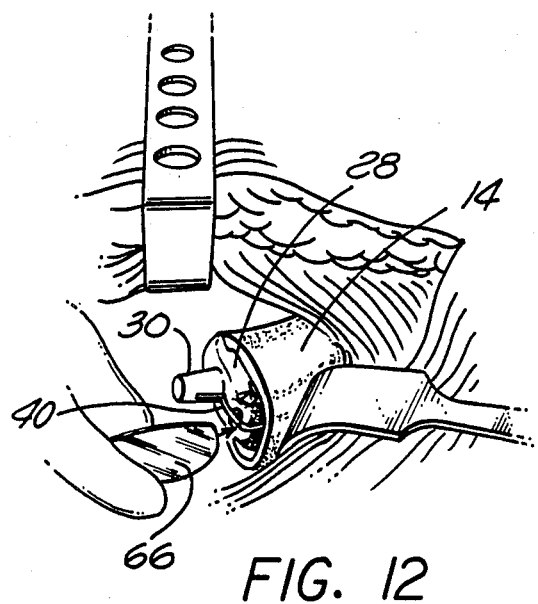
FIG. 12 is an enlarged and fragmented perspective view showing placement of an antirotation fin into the implanted femoral component.
Figure 10:
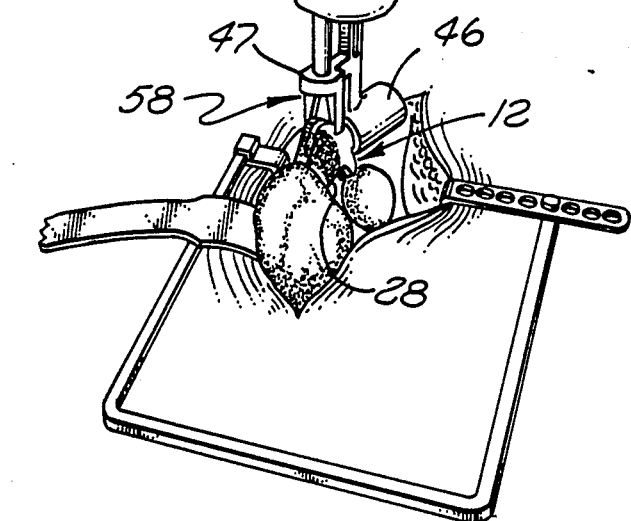
FIG. 10 is an enlarged sectional view illustrating the femoral component installed into the femur of a patient, with a portion of the femoral component held in a reduced size configuration.
Figure 11:
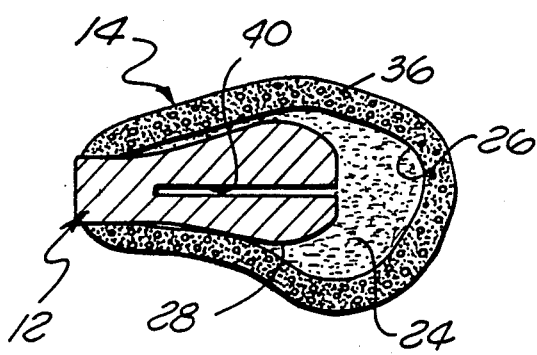
FIG. 11 is an enlarged sectional view similar to FIG. 10 but depicting the implanted femoral component in a expanded size configuration.
Figure 12:
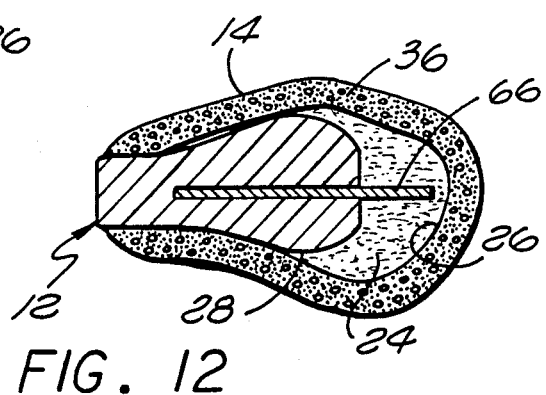

With the femoral component 12 securely engaged and held in the reduced size configuration, as shown in FIG. 8, the prosthesis can be implanted quickly and easily into the prepared, resected femur 14. Such implantation may include, if desired, appropriate use of a mallet 64 (FIG. 9) to position the prosthesis in the final seated position within the medullary canal 26, with the neck 30 projecting upwardly from the femur 14 (FIG. 12) for appropriate mounting of the ball-shaped head 32. When the final seated position is reached, the installation tool 42 is released from the prosthesis and removed. This permits the upper region 28 of the prosthesis to expand from the reduced profile configuration shown in FIG. 10 back to the normal nondeformed state shown in FIG. 11. In the nondeformed state, the mechanical press-fit lock with the patient bone is substantially enhanced.

The stability of the implanted femoral component 12 is further enhanced by placement of an antirotation fin or shim 66 into the slot 40 which is at least partially exposed from the upper end of the prosthesis. More specifically, as viewed in FIGS. 12 and 13, the antirotation fin 66 is inserted to fill the slot 40 and thereby prevent postoperative return movement of the prosthesis to the compressed state in response to loads encountered upon patient movements. Such filling of the slot 40 beneficially maintains the prosthesis in locked relation to patient bone to prevent prosthesis movements rotationally, longitudinally, etc. Moreover, in the preferred form, the antirotation fin 66 in sized to extend at least a short distance beyond the lateral side edge of the prosthesis to lock within patient cancellous bone 24, as shown in FIG. 13, for further enhanced rotational stability.

In another form of the invention, as viewed in FIGS. 14–20, the improved acetabular component 16 is provided for secure implantation into a patient's acetabulum 18. The acetabular component 16 is also designed for assuming a relatively reduced profile size for facilitated implantation, after which the acetabular component is slightly expanded for a stable and tight fit with patient bone without requiring bone cement for affixation. If desired, in the case of a total hip joint replacement, the acetabular component 16 can be used in combination with the femoral component 12 described previously herein.

Figure 14:
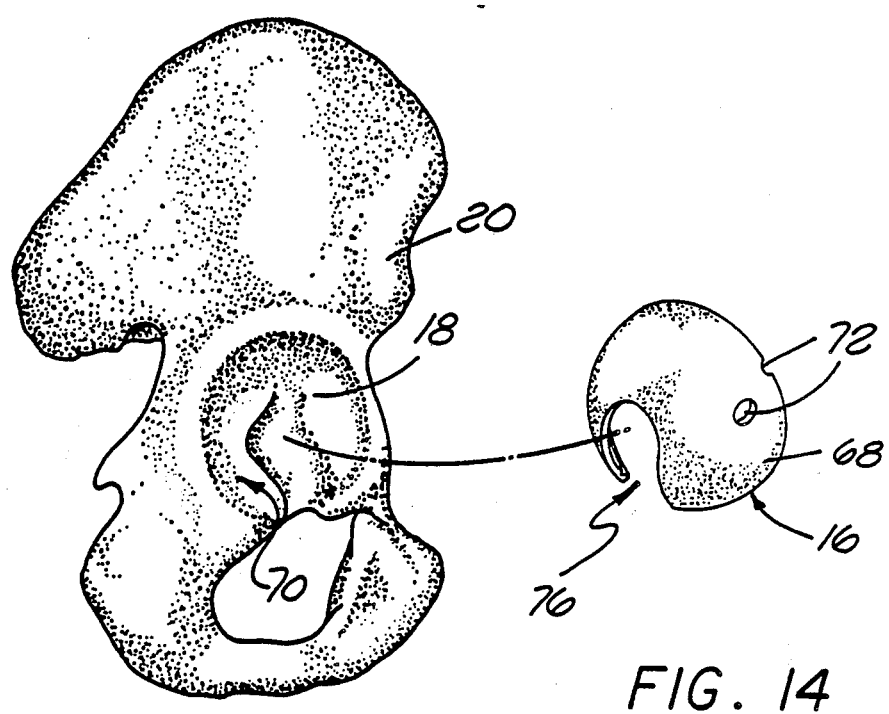
FIG. 14 is an exploded perspective view illustrating an acetabular component for installation into the acetabulum of a patient.
Figure 15:
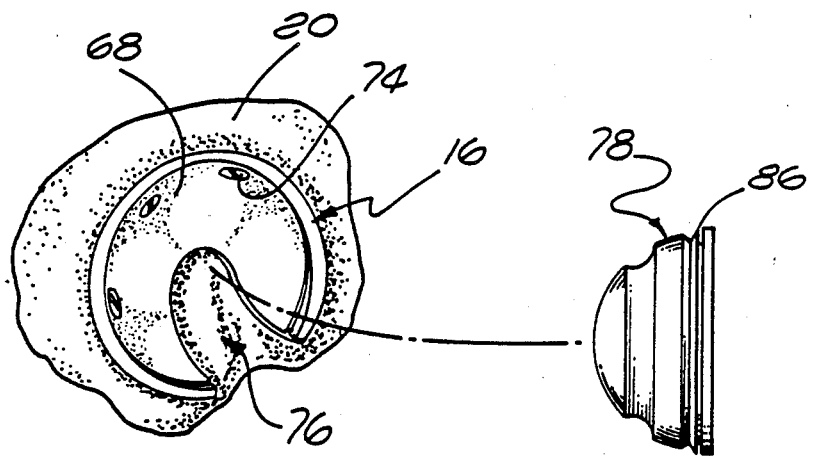
FIG. 15 is an enlarged exploded perspective view showing an acetabular bearing member for seated placement into an implanted acetabular component.

As shown in FIGS. 14 and 15, the acetabular component 16 comprises a generally hemispherical shell-shaped cap 68 having an external part-spherical surface which may be coated in selected areas with a porous bone ingrowth material, as previously described. The component material is again chosen to be relatively rigid, such as titanium or a titanium alloy, to exhibit a high degree of structural strength in combination with a high degree of elasticity when deformed. In this case, however, the part-spherical external surface of the acetabular component is formed on a radius to fit relatively snugly but easily onto a prepared acetabulum platform 70 shown in FIG. 14 to have a generally horseshoe-shaped configuration. One or more open ports 72 may also be formed in the component 16 to permit passage of bone screws 74 (FIG. 15) used to anchor the component more securely to the patient bone.

The acetabular component 16 has a radial segment thereof removed or relieved as depicted by arrow 76 (FIGS. 14 and 15) to form the component into a generally horseshoe-shaped geometry. With this configuration, the acetabular component 16 can be seated firmly on the acetabular platform 70 with the open segment 76 of the component 16 aligned with the corresponding open segment of the platform 70. Importantly, this relieved or open segment 76 in the acetabular component 16 permits the component 16 to be expanded slightly into a tight press fit engagement with patient bone within acetabulum 18, as will be described.

The desired slight expansion of the acetabular component 16 is achieved by inserting a generally hemispherical shaped bearing member 78 which is slightly oversized into the acetabular component 16. More particularly, as viewed in FIGS. 15–20, the bearing member 78 has an external surface 80 formed at least in part on a radius 82 which is slightly larger, such as by a few thousandths of an inch, than a corresponding radius 84 defining an inner part-spherical surface 85 on the acetabular component 16. The bearing member 78, which is formed from a standard plastic bearing material of the type used in prosthetic devices, is then press-fit into the implanted acetabular component 16. An external snap rib 86 on the bearing member 78 snaps into engagement with an internal snap groove 88 on the component 16 when the bearing member is fully seated. Importantly, when full seating of the bearing member is achieved, the acetabular component 16 is subjected to substantial radial expansion forces to expand the component 16 tightly against the acetabular platform 70.

After full implantation of the acetabular component 16 and its associated bearing member 78 together with the femoral component 12, the resultant hip prosthesis 10 can be assembled by fitting the ball-shaped head 32 on the femoral component 12 into a matingly shaped socket 90 formed in the bearing member 78. The surgical site may then be closed according to conventional medical procedures. The resultant prosthetic hip joint 10 will function postoperatively to accommodate the various mechanical loads imposed by patient movements without risk of the prosthetic components working loose with respect to patient bone over a prolonged service life.

A variety of modifications and improvements to the prosthetic hip joint of the present invention will be apparent to those skilled in the art. For example, various femoral and acetabular component geometries can be used while incorporating the basic expansion capabilities described herein with respect to the invention. As one illustrative example, a variety of femoral component shape variations can be used having contoured or integrally ribbed surfaces designed for improved bone interlock, wherein such integral surfaces cooperate with the fin 66 and slot 40 described herein to achieve a highly stable prosthesis fit. Accordingly, no limitation on the invention is intended by way of the above description and accompanying drawings, except as set forth in the appended claims.

What is claimed is:

1. A hip prosthesis for implantation into the upper end of the medullary canal of a resected femur, said prosthesis comprising:
a femoral component having an elongated stem and a neck member projecting upwardly from the stem, said femoral component having a size and shape to tightly fit into the medullary canal of a resected femur, said femoral component having a longitudinally elongated slot formed therein and opening outwardly and upwardly when said femoral component is implanted into the femur;
said femoral component being formed from a relatively rigid material having a high degree of elasticity, said femoral component being deformable to a reduced size profile for facilitated implantation into the medullary canal by pressing inwardly on opposite sides of said femoral component at opposite sides of said slot such that at least a portion of said slot is reduced in width, said femoral component being releasable after implantation and thereupon returning substantially to its initial nondeformed state in tight press-fit engagement with the femur; and
an antirotation fin having a size and shape to be disposed within said slot after said femoral component is implanted into the femur, said fin substantially filling said slot to prevent return movement of said femoral component to said reduced size profile.

2. The hip prosthesis of claim 1 wherein said femoral component is formed from a titanium based material.

3. The hip prosthesis of claim 1 wherein said femoral component includes an elongated lower stem joined to an enlarged upper region sized cooperatively to fit with relatively close tolerance into the upper end of the resected femur, said slot being formed in said enlarged upper region.

4. The hip prosthesis of claim 3 wherein said slot is formed to open upwardly and in a laterally outwardly direction when said femoral component is implanted into the resected femur.

5. The hip prosthesis of claim 4 wherein said antirotation fin has a size and shape to protrude outwardly from the slot beyond an outer perimeter of the prosthesis to bridge at least partially into adjacent patient bone.

6. The hip prosthesis of claim 3 further including a neck member projecting upwardly from said upper region of said femoral component, and a generally ball-shaped head for mounting onto said neck member.

7. The hip prosthesis of claim wherein said femoral component includes a porous ingrowth surface coating at least a portion of the exterior thereof.

8. The hip prosthesis of claim further including an acetabular component for implantation into the acetabulum of a patient, said acetabular component comprising a generally hemispherically shaped cap having a size for facilitated implantation into the patient's acetabulum, said cap defining a relieved radial segment to permit expansion of said cap to an increased diametric size, and means for expanding said cap to the increased diametric size after implantation into the patient's acetabulum for tight press-fit fixation of said acetabular component therein.

9. The hip prosthesis of claim 8 wherein said expanding means comprises generally a hemispherically shaped bearing member.

10. A hip prosthesis for implantation into the upper end of a medullary canal of a resected femur, said prosthesis comprising:
a femoral component having an elongated lower stem joined to an enlarged upper region formed cooperatively to have a size and shape to tightly fit into the medullary canal, said upper region having a longitudinally elongated slot formed therein and opening laterally and upwardly of said enlarged region, said femoral component further including a neck member projecting upwardly from said upper region;
said femoral component being formed from a relatively rigid material having a high degree of elasticity, said femoral component being deformable to ar educed size profile to permit facilitated implantation thereof into the resected femur by squeezing said upper region inwardly inn the anterior-posterior direction at opposite sides of said slot to reduce at least a portion of said slot in width, said upper region being releasable after implantation and thereupon returning substantially to its nondeformed state for tight press fit engagement with the femur; and
an antirotation fin sized to fit into said slot, said fin disposed within said femoral component after said femoral component is implanted into the femur, said fin extending outwardly from said enlarged region bridging along the lateral side of the femoral component into adjacent patient bone.

11. The hip prosthesis of claim 10 wherein said femoral component has an outer surface coated at least in part with a porous bone ingrowth material.

12. In combination:
a hip prosthesis for implantation into the upper end of the medullary canal of a resected femur, said prosthesis comprising a femoral component having an elongated stem and a neck member projecting upwardly from the stem, said femoral component having a size and shape to tightly fit into the medullary canal of a resected femur, said femoral component having a longitudinally elongated slot formed therein and opening outwardly and upwardly when said femoral component is implanted into the femur, said femoral component being formed from a relatively rigid material having a high degree of elasticity, said femoral component being deformable to a reduced size profile by pressing inwardly on opposite sides thereof at opposite sides of said slot for facilitated implantation into the medullary canal, said femoral component being releasable after implantation and thereupon returning substantially to its initial nondeformed state in tight press-fit engagement with the femur, and an antirotation fin having a size and shape to be disposed within said slot after said femoral component is implanted into the femur, said fin substantially filling said slot to prevent return movement of said femoral component to said reduced size profile; and
means for clamping said femoral components to the reduced size profile during implantation and for unclamping said femoral component after implantation.

13. In combination:

a hip prosthesis for implantation into the upper end of a medullary canal of a resected femur, said prosthesis comprising a femoral component having an elongated lower stem joined to an enlarged upper region formed cooperatively to have a size and shape to tightly fit into the medullary canal, said upper region having a longitudinally elongated slot formed therein and opening laterally and upwardly of said enlarged region, said femoral component further including a neck member projecting upwardly from said upper region, said femoral component being formed from a relatively rigid material having a high degree of elasticity, said femoral component being deformable to a reduced size profile to permit facilitated implantation thereof into the resected femur by squeezing said upper region inwardly in the anterior-posterior direction at opposite sides of said slot to reduce at least a portion of said slot in width, said upper region being releasable after implantation and thereupon returning substantially to its nondeformed state of tight press fit engagement with the femur, and an antirotation fin sized to fit into said slot, said fin being disposed within said femoral component after said femoral component is implanted into the femur, said fin extending outwardly from said enlarged region bridging along the lateral side of the femoral component into adjacent patient bone; and means for clamping the femoral component to the reduced size profile during implantation and for unclamping the femoral component after implantation.

* * * * *